United States Patent [19]

Fortier

[11] Patent Number: 5,532,009
[45] Date of Patent: Jul. 2, 1996

[54] FAT SUBSTITUTES CONTAINING WATER SOLUBLE BETA-CAROTENE

[75] Inventor: Nancy E. Fortier, Cincinnati, Ohio

[73] Assignee: The Procter & Gamble Company, Cincinnati, Ohio

[21] Appl. No.: 473,889

[22] Filed: Jun. 7, 1995

[51] Int. Cl.⁶ .................................................. A23D 7/005
[52] U.S. Cl. ........................................... 426/73; 426/611
[58] Field of Search ............................ 426/73, 611, 601

[56] References Cited

U.S. PATENT DOCUMENTS

| | | | |
|---|---|---|---|
| 2,855,306 | 10/1958 | Rosenberg | 99/2 |
| 3,657,424 | 4/1972 | Aktins et al. | 424/153 |
| 4,005,196 | 1/1977 | Jandacek et al. | 424/180 |
| 4,034,083 | 7/1977 | Mattson | 424/180 |
| 4,285,981 | 8/1981 | Todd et al. | 426/250 |
| 4,315,947 | 2/1982 | Todd et al. | 426/250 |
| 4,316,917 | 2/1982 | Antoshkiw et al. | 426/540 |
| 4,880,657 | 11/1989 | Guffey et al. | 426/601 |

FOREIGN PATENT DOCUMENTS

| | | | |
|---|---|---|---|
| 0154368 | 9/1985 | European Pat. Off. | A23K 1/100 |
| 0285682 | 10/1988 | European Pat. Off. | A61K 9/16 |
| 0415464A2 | 3/1991 | European Pat. Off. | A23D 9/00 |
| WO92/10941 | 7/1992 | European Pat. Off. | A23D 9/00 |
| 990902 | 5/1965 | Switzerland | A61K 3/10 |

OTHER PUBLICATIONS

Chemical Abstracts 116:19966.
Chemical Abstracts 113:130922.
Chemical Abstracts 109:110847.
Chemical Abstracts 123:296447.
Chemical Abstracts 123:122762.
Chemical Abstracts 121:65560.
Chemical Abstracts 121:7844.
Chemical Abstracts 110:7320.

*Primary Examiner*—Carolyn Paden
*Attorney, Agent, or Firm*—R. A. Dabek; J. C. Rasser

[57] ABSTRACT

The present invention relates to non-absorbable, non-digestible fat compositions fortified with a water soluble carotenoid/cyclodextrin complex. The compositions are useful as fat substitutes in food and pharmaceutical compositions. The carotenoid is readily bioavailable and resists partitioning into the fat/fat-like phase.

4 Claims, No Drawings

FAT SUBSTITUTES CONTAINING WATER SOLUBLE BETA-CAROTENE

FIELD OF THE INVENTION

The present invention relates to edible fat-containing food products comprising a non-digestible fat and a water soluble beta-carotene. More particularly, the present invention relates to a composition comprising non-absorbable, non-digestible fats and water soluble beta-carotene wherein the beta-carotene has increased bioavailability.

BACKGROUND OF THE INVENTION

High blood cholesterol (hypercholesterolemia) is recognized as being a risk factor in cardiovascular disease which comprises a major health care problem today. Epidemiological studies have demonstrated that, with few exceptions, populations consuming large quantities of saturated fat and cholesterol have a relatively high concentration of serum cholesterol and a high mortality rate from coronary heart disease. A regimen for alleviating or preventing hypercholesterolemia is to reduce fat intake by using reduced calorie fats or a fat substitute (i.e. non-absorbable, non-digestible fat), in particular, polyol fatty acid polyesters, and more specifically the sugar fatty acid polyesters.

While desired for treating hypercholesterolemia, the sugar fatty acid polyesters interfere with the body's absorption of fat soluble vitamins, see for example U.S. Pat. No. 4,005,196 and U.S. Pat. No. 4,034,083. Any oil soluble vitamins which are dissolved in the sugar fatty acid polyesters are lost when the nondigestible fat passes through the digestive track.

Heretofore, the composition containing sugar fatty acid polyesters are fortified with increased levels of the fat soluble vitamins to overcome possible vitamin malabsorption. However, higher vitamin fortification levels can impart taste, odor and color negatives to the product. For example U.S. Pat. No. 5,248,504 discloses a product containing oil-soluble vitamins, digestible fat and indigestible polyol fatty acid polyesters which comprises two distinct fat phases, A and B, both of which contain a fat soluble vitamin. The fat phase (B) contains an oil-soluble vitamin at a concentration level that is at least twice as high as the concentration level of fat phase (A). Further, fat phase (A) comprises indigestible polyol fatty acid polyesters, which have been shown to interfere with the absorption of oil-soluble vitamins. It has also been taught, see for example EPO 415,464A2, to use compounds which have reduced hydrophobicity. Although reducing hydrophobicity may reduce the loss of oil soluble vitamins, the vitamins are still essentially water-insoluble.

An important fat-soluble vitamin is vitamin A. Beta-carotene is a well known vitamin A precursor and is the most commonly used source of vitamin A for nutritional supplementation. Beta-carotene is also reported to protect cells from free radicals that may induce cancer and atherosclerosis.

The present invention relates to a combination of non-absorbable and non-digestible fat and water-soluble beta carotene. The loss of the oil soluble vitamins can be overcome by adding beta-carotene of the type disclosed hereinafter to fat substitutes, or to foods containing these fat substitutes. The present invention, the beta-carotene is complexed with cyclodextrin, resulting in a water soluble beta-carotene. While not wishing to be bound by theory, it is believed that the beta-carotene complex prefers the aqueous phase in the body rather than the fat or fat-like phase. It therefore becomes more bioavailable, i.e., it does not leave the body with the non-digestible, non-absorbable fat and can therefore be utilized by the body. Fortification of products containing the non-digestible, non-absorbable fat with the water-soluble, bioavailable form of beta-carotene requires a lower usage level of the vitamin precursor to offset the effects of lowered serum levels, thus reducing the cost of fortification. Because the beta-carotene is encapsulated the color, flavor and stability negatives associated with high vitamin usage levels are minimized.

SUMMARY OF THE INVENTION

The present invention relates to non-absorbable, non-digestible fat compositions fortified with a water soluble carotenoid/cyclodextrin complex. The compositions are useful as fat substitutes in food and pharmaceutical compositions. The carotenoid is readily bioavailable and resists partitioning into the fat phase. This benefit is achieved by formulating compositions comprising a polyol fatty acid polyester and a complexed carotenoid/cyclodextrin powder.

DETAILED DESCRIPTION OF THE INVENTION

The compositions of the present invention may consist of a non-digestible fat or a mixture of non-digestible fats or a combination of non-digestible fats and natural or synthetic triglycerides, and a water soluble carotenoid/cyclodextrin complex.

The preferred fat substitutes are polyol fatty acid polyesters.

Polyol Fatty Acid Polyesters

By "polyol" is meant a polyhydric alcohol containing at least 4, preferably from 4 to 12, and, most preferably from 6 to 8, hydroxyl groups. Polyols include monosaccharides, disaccharides and trisaccharides, sugar alcohols other sugar derivatives (e.g., alkyl glycosides), polyglycerols (e.g., diglycerol and triglycerol), pentearythritol, and polyvinyl alcohols. Preferred polyols include xylose, arabinose, ribose, xylitol, erythritol, glucose, methyl glucoside, mannose, galactose, fructose, sorbitol, maltose, lactose, sucrose, raffinose, and maltotriose. Sucrose is an especially preferred polyol.

By "polyol polyester" is meant a polyol having an average of at least 4 ester groups. It is not necessary that all of the hydroxyl groups of the polyol be esterified, however disaccharide polyesters should have no more than 3 on average, and more preferably no more than 2 unesterified hydroxyl groups. Typically, substantially all (e.g., at least about 85%) of the hydroxyl groups of the polyol are esterified. In the case of sucrose polyesters, typically from about 7 to 8 of the hydroxyl groups of the polyol are esterified.

Fatty acids and/or other organic radicals having at least 2 carbon atoms and up to 30 carbon atoms can be used to esterify the polyol. Typically they contain from 8–24 carbon atoms, and more typically at least 12–18 carbon atoms. The acid radicals can be saturated or unsaturated, including positional or geometrical isomers, e.g. cis- or trans-isomers, straight chain or branched chain aliphatic or aromatic, and can be the same for all ester groups, or can be mixtures of different acid radicals. Cyclic aliphatics such as cyclohexane carboxylic and polymeric ester-forming radicals such as polyacrylic and dimer fatty acid can also be used to esterify the polyol.

Liquid polyol polyesters and non-digestible oils have a complete melting point below about 37° C. Suitable liquid non-digestible edible oils for use herein include liquid polyol polyesters (see Mattson & Volpenhein, U.S. Pat. No. 3,600,186 issued Aug. 17, 1971, Jandacek; U.S. Pat. No. 4,005,195; Issued Jan. 25, 1977); liquid esters of tricarballylic acids (see Hamm; U.S. Pat. No. 4,508,746; Issued Apr. 2, 1985); liquid diesters of dicarboxylic acids such as derivatives of malonic and succinic acid (see Fulcher, U.S. Pat. No. 4,582,927; Issued Apr. 15, 1986); liquid triglycerides of alpha-branched chain carboxylic acids (see Whyte; U.S. Pat. No. 3,579,548; Issued May 18, 1971); liquid ethers and ether esters containing the neopentyl moiety (see Minich; U.S. Pat. No. 2,962,419; Issued Nov. 9, 1960); liquid fatty polyethers of polyglycerol (See Hunter et al; U.S. Pat. No. 3,932,532; Issued Jan. 13, 1976); liquid alkyl glycoside fatty acid polyesters (see Meyer et al; U.S. Pat. No. 4,840,815; Issued Jun. 20, 1989); liquid polyesters of two ether linked hydroxypolycarboxylic acids (e.g., citric or isocitric acid) (see Huhn et al; U.S. Pat. No. 4,888,195; Issued Dec. 19, 1988); and liquid esters of epoxide-extended polyols (see White et al; U.S. Pat. No. 4,861,613; Issued Aug. 29, 1989); as well as liquid polydimethyl siloxanes (e.g., Fluid Silicones available from Dow Corning).

Preferred liquid non-digestible oils are sugar polyesters, sugar alcohol polyesters, and mixtures thereof, preferably esterified with fatty acids containing from 8 to 26 carbon atoms, and most preferably with fatty acids having 8 to 18 carbon atoms. Those which have minimal or no solids at body temperature (i.e., 98.6° F., 37° C.) usually contain ester groups having a high proportion of $C_{12}$ or lower fatty acid radicals or else a high proportion of $C_{18}$ or higher unsaturated fatty acid radicals. Preferred unsaturated fatty acids in such liquid polyol polyesters are oleic acid, linoleic acid, and mixtures thereof.

Non-digestible polyol polyester hardstock or solid materials suitable for use herein can be selected from solid sugar polyesters, solid sugar alcohol polyesters and mixtures thereof, and contain ester groups, e.g. generally 5 to 8 ester groups, which consist essentially of long chain saturated fatty acid radicals. Suitable saturated fatty acid radicals contain at least 14, preferably from 14 to 26, most preferably from 16 to 22, carbon atoms. The long chain saturated fatty acid radicals can be used singly or in mixtures with each other. In addition, straight chain (i.e. normal) fatty acid radicals are typical for the long chain saturated fatty acid radicals.

Certain intermediate melting polyol fatty acid polyesters have been developed that have a specific rheology that defines their physical properties, i.e., their melting points, viscosity, and shear viscosities and crystal size and shape are also useful. (See Bernhardt; European Patent Application Nos. 236,288 and 233,856; Published Sep. 9, and Aug. 26, 1987, respectively.) These intermediate melting polyol polyesters are viscous and have a high liquid/solid stability at body temperature. An example of such intermediate melting polyol polyesters are those obtained by substantially completely esterifying sucrose with a 55:45 mixture of fully hydrogenated and partially hydrogenated soybean oil fatty acid methyl esters. These polyol polyesters are most preferred for products in which a high level of solids is required to provide stability, e.g. shortening, pastries, chocolate, crackers, etc.

Blends of liquid polyol polyesters with completely solid polyol polyester hardstocks, preferably esterified with $C_{10}$–$C_{22}$ saturated fatty acids (e.g. sucrose octastearate), can be solid or semi-solid at room temperature. (See, for example, Jandacek; U.S. Pat. No. 4,005,195; and Jandacek/Mattson; U.S. Pat. No. 4,005,196; Both issued Jan. 25, 1977.)

Liquid or solid polyol polyesters can be prepared by a variety of methods known to those skilled in the art. These methods include: transesterification of the polyol (i.e. sugar or sugar alcohol) with methyl, ethyl or glycerol esters containing the desired acid radicals using a variety of catalysts; acylation of the polyol with an acid chloride; acylation of the polyol with an acid anhydride; and acylation of the polyol with the desired acid, per se. (See, for example, U.S. Pat. Nos. 2,831,854, 3,600,186, 3,963,699, 4,517,360 and 4,518,772, all of which are incorporated by reference. These patents all disclose suitable methods for preparing polyol polyesters.)

When making mixtures of liquid and solid non-digestible and non-absorbable materials, the non-digestible particles can be dispersed as discrete, unaggregated entities in the liquid non-digestible oil. However, these non-digestible particles can also cluster together to form much larger aggregates which are dispersed in the liquid non-digestible oil. This is particularly true of those non-digestible particles that are platelet-like in form. Aggregates of platelet-like non-digestible particles are typically porous in character and thus capable of entrapping significant amounts of liquid non-digestible oil.

Solid non-digestible particles can be used alone or dispersed in the non-digestible liquid oil component.

Diversely Esterified Polyol Polyesters

"Diversely esterified polyol polyesters" contain two basic types of ester groups: (a) groups formed from long chain saturated fatty acids radicals, and (b) groups formed from acid radicals which are "dissimilar" to these long chain saturated fatty acid radicals.

Suitable long chain saturated fatty acid radicals contain from 20 to 30, most preferably 22–26, carbon atoms. The long chain saturated fatty acid radicals can be used singly, or in mixtures with each other, in all proportions. Usually, straight chain (i.e. normal) fatty acid radicals are used.

The dissimilar radicals can comprise $C_{12}$ or higher unsaturated fatty acid radicals or $C_2$–$C_{12}$ saturated fatty acid radicals or mixtures thereof, or can be fatty-fatty acid radicals, aromatic acid radicals, or ultra-long chain fatty acids or various branched cyclic or substituted acid radicals.

Preferred "dissimilar" acid radicals comprises long chain unsaturated fatty acid radicals, containing at least 12, preferably from 12 to 26, more preferably from 18 to 22 carbon atoms and short chain saturated fatty acid radicals having from 2 to 12 and preferably from 6 to 12 carbon atoms and mixtures thereof.

Fatty-fatty acid radicals are a fatty acid radical having at least one hydroxyl group that is itself esterified with another fatty acid or other organic acid. Ricinoleic acid is a preferred hydroxy-fatty acid. Sources of hydroxy-fatty acids include hydrogenated castor oil, strophanthus seed oils, calendula officinalis seed oils, hydrogenated strophanthus seed oils and hydrogenated calendula officinal is seed oils, cardamine impatiens seed oils, kamala oils, mallotus discolor oils, and mallotus claoxyloides oils.

Hydroxy fatty acids can also be synthetically prepared by oxidative hydroxylation of unsaturated fatty acids using oxidizing agents such as potassium permanganate, osmium tetroxide, and peracids such as peracetic acid. Using this method, 9, 10-dihydroxy-octadecanoic acid can be made from oleic acid, and 9, 10, 12, 13-tetrahydroxy-octadecanoic acid can be made from linoleic acid. Another way to prepare hydroxy fatty acids, such as 10-hydroxy-12-cis-octadecenoic and 10-hydroxy-12 cis, 15-cis-octadecanoic acids, synthetically is by conversion of fatty acids such as linoleic and linolenic via microorganisms such as Nocardia Cholesteroliim.

The same fatty acid sources used for esterification of the polyols can be used for esterification of the hydroxyl group of the hydroxy-fatty acid radical. These include aromatic acids such as benzoic or toluic; branched chain radicals such as isobutyric, neoctanoic or methyl stearic acids; ultra-long chain saturated or unsaturated fatty acid radicals, such as tricosanoic or tricosenoic; cyclic aliphatics such as cyclohexane carboxylic; and polymeric ester-forming radicals such as polyacrylic and dimer fatty acid.

Aromatic acid radicals can also be used as a dissimilar ester group. A wide variety of aromatic compounds including benzoic compounds such as benzoic or toluic acid; amino benzoic compounds such as amino benzoic and aminomethyl benzoic acids; hydroxybenzoic compounds such as hydroxybenzoic, vanillic and salicylic acids; methoxybenzoic compounds such as anisic acid; acetoxyphenylacetic compounds such as acetyl mandelic acid; and halobenzoic compounds such as chlorobenzoic, dichlorobenzoic, and fluorobenzoic acids; acetyl benzoic, cumic, phenylbenzoic, and nicotinic; and polycyclic aromatic radicals including fluorene carboxylic can be used singly, or in mixtures with each other, in all proportions.

Various other ester-forming radicals can also serve as those which form the dissimilar ester groups of the diversely esterified polyol polyester particles used herein. Such other radicals can be branched alkyl chain; ultra-long chain saturated or unsaturated radicals; cyclic aliphatic radicals including cyclobutane carboxylic, cyclopentane carboxylic, cyclohexane carboxylic, cyclohexane acetic, and hydroxycyclic such as ascorbic; polycyclic aliphatic such as abietic acid; polymeric ester-forming radicals such as polyacrylic and dimer fatty acid; and alkyl chain radicals containing halogen amino or aryl groups.

The diversely esterified polyol polyesters can be prepared by esterifying the desired polyol with the requisite type of ester-forming radicals by the methods described for making polyol polyesters. When using a methyl ester route to prepare these diversely esterified solid polyol polyesters having mixed dissimilar acid radicals and long chain saturated fatty acid radicals, the octaester of one of the types of acids (e.g., dissimilar acids, or long chain saturated fatty acids) can be prepared first, followed by partial interesterification of this initial reaction product with the methyl ester of the other type of acid.

These polyol polyesters are particularly useful where lower solids levels are desirable since they are less waxy.

Polyol Polyester Polymers

Other solid non-digestible polyol polyesters comprise polyol polyester polymers. Polyol polyester polymers are formed by polymerizing a polyol polyester monomer to provide a molecule having at least two separate esterified polyol moieties linked by covalent bonds between the fatty acid radicals. For example, two sucrose octabehenate monomers could be cross-linked between fatty acids to form a polymer. Repeating units of such polyol polyester polymers can be the same or different such that the generic term "polymer" in this context includes the specific term "copolymer". The number of repeating monomer (or co-monomer) units which make up such polyol polyester polymers can range from about 2 to 20, preferably from about 2 to 12. Depending on the method of preparing them, the polyol polyester polymers are frequently oligomers containing from 2 to 4 monomeric units, i.e., dimers, trimers, or tetramers.

The most preferred polyol polyester polymers are sucrose polyester polymers having a number average molecular weight of from about 4000 to about 60,000, preferably from about 4000 to about 36,000, more preferably from about 5000 to about 12,000.

One way to prepare solid polyol polyester polymers is by polymerizing polyol polyesters using well known methods, including, but not limited to, photochemical reactions and reactions with transition metal ions, heat, or free radical initiators such as di-tert-butyl peroxide.

Alternatively, polyol polyester polymers can be prepared directly by esterifying and/or interesterifying the polyol material with polybasic polymerized fatty acids or their derivatives. For example, the polyol polyester polymers could be prepared by reacting the acid chlorides or acid anhydrides of the desired polymer acids with sucrose, preferably using a sequential esterification process. Polyol polyester polymers can also be prepared by reacting methyl esters of the desired polymer acids with sucrose in the presence of a fatty acid soap and a basic catalyst such as potassium carbonate.

Common examples of polymerizable acids are those containing two or more double bonds (polyunsaturated acids) such as the linoleic acid, linolenic and eleostearic acids, parinaric acid, eicosadienoic acid, eicosatetraenoic acid arachidonic acid, 5,13-docosadienoic acid and clupanodonic acid. Monounsaturated fatty acids, such as oleic, elaidic and erucic acids, can also be used in preparing suitable long chain fatty acid dimers which in turn can then be used to form the solid polyol polyester polymers. Preferred polybasic polymerized fatty acids and fatty acid derivatives for use in preparing polymer-containing polyol polyesters include dibasic acids produced by dimerization of the fatty acids or fatty acid lower esters derived from polyunsaturated vegetable oils such as soybean oil or cottonseed oil or from animal fats such as tallow.

All of the foregoing types of polybasic polymerized fatty acids may themselves be made by a variety of methods known to those skilled in the art. (See Lutton; U.S. Pat. No. 3,353,967; Issued Nov. 21, 1967, Goebel; U.S. Pat. No. 2,482,761; Issued Sep. 27, 1949, Harrison et al; U.S. Pat. No. 2,731,481; Issued Jan. 17, 1956 and Barrett et al; U.S. Pat. No. 2,793,219; Issued May 21, 1957, all of which are incorporated herein by reference.)

Polyglycerol Esters

A third type of non-digestible solid is polyglycerol ester. Polyglycerol esters contain at least about 2 glycerol moieties, preferably from about 3 to 10 glycerol moieties, even most preferably from 4 to 8 glycerol moieties. The distribution of the number of glycerol moieties in such polyglycerol ester mixture may be narrow or broad. Typically at least about 30% of the hydroxyl groups of the polyglycerol are esterified with fatty acids. Preferably at least about 50% of the hydroxyl groups are esterified with long chain ($C_{16}$–$C_{26}$) fatty acid radicals with at least 40% of these long chain fatty acids being saturated and having at least 18 carbon atoms. Preferably, at least about 50%, and more preferably at least 75% of the long chain fatty acids are saturated and have at least 18 carbon atoms. The polyglycerol esters preferably have an Iodine Value of less than 50, preferably less than about 20, and most preferably less than about 5.

The solid polyglycerol ester materials can be made according to the same known methods for preparing polyol polyesters.

Co-crystallized Blend of Hardstock and Crystal Modifier

A co-crystallized blend of: (1) a polyol polyester hardstock, i.e., a solid, usually saturated polyol polyester; and (2) a crystal modifier can also be used. The particular ratio of hardstock to crystal modifier depends upon the specific hardstock and/or crystal modifier selected and the specific solid properties desired. Preferably, the ratio of hardstock to crystal modifier is from about 95:5 to about 25:75, more preferably from about 90:10 to about 40:60, and most preferably from about 80:20 to about 60:40.

The solid polyol fatty acid polyester hardstocks useful in forming the co-crystallized blends are those which are solid at temperatures of about 37° C. and higher, preferably about 50° C. and higher, and most preferably about 60° C. or higher. Crystal modifier material can comprise any material which is capable of inducing the solid polyol polyester hardstock materials to form smaller particles, when co-crystallized in a liquid non-digestible oil.

Examples of suitable types of crystal modifiers include the diversely esterified polyol polyesters, the polyol polyester polymers, polyglycerol esters and other materials such as fatty acid monoglycerides, naturally occurring waxes with long chain alkyl or ester groups, paraffinic hydrocarbon microcrystalline waxes and long chain alcohols. Preferred are monoglycerides containing $C_{18}$ and higher saturated fatty acids. Monobehenin is particularly preferred. A preferred naturally occurring wax material is beeswax. Beeswax consists largely of myricyl palmitate, cerotic acid and esters and some high carbon paraffins.

Specific examples of suitable crystal modifier-type polyol polyesters include sucrose tetrabehenate tetracaprylate, sucrose pentabehenate trilaurate, sucrose hexabehenate dicaprylate, sucrose hexabehenate dilaurate. Other examples include the sorbitol hexaester of palmitoleic and arachidic fatty acid radicals in a 1:2 molar ratio, the raffinose octaester of linoleic and behenic fatty acid radicals in a 1:3 molar ratio, the maltose heptaester of a mixture of sunflower oil and lignoceric fatty acid radicals in a 3:4 molar ratio, the sucrose octaester of oleic and behenic fatty acid radicals in a 2:6 molar ratio, the sucrose octaester of lauric, linoleic and behenic fatty acid radicals in a 1:3:4 molar ratio, and the sucrose hepta- and octaesters of $C_{18}$ mono- and/or di-unsaturated fatty acid radicals and behenic fatty acid radicals in a molar ratio of unsaturated:behenic acid radicals of about 1:7 to 3:5.

Conventional Fats

The compositions of the present invention may additionally contain natural or synthetic fats or oils. Oils or triglycerides for use herein include, partially or fully hydrogenated, coconut oil, palm kernel oil, palm oil, marine oils, lard, tallow, butter fat, cocoa butter fat, soybean oil, safflower oil, cotton seed oil, rapeseed oil, corn oil, sunflower oil, canola oil and mixtures thereof. The total amount of these natural or synthetic fats or oils used will depend somewhat on the total amount of fat reduction desired.

Beta-Carotene/Cyclodextrin Complex

Beta-Carotene

Beta-carotene is a naturally occurring precursor to vitamin A and it's often used as an orange/yellow pigment. The molecular structure is similar to that of Vitamin A. Beta-carotene is typically derived by extraction from plant sources such as algae. The extraction processes are well known in the art. Beta-carotene may also be synthesized using known chemical processes such as that disclosed in U.S. Pat. No. 4,504,499. Beta-carotene is easily degraded when subjected to air, UV light or high temperatures. Therefore, beta-carotene is generally sold in stabilized forms. Stabilized beta-carotene is readily available from several commercial sources, for example, BASF Corporation and Hoffman LaRoche, Nutley, N.J. In the practice of the present invention, it is preferred to use neat beta-carotene crystals, available only through special arrangement with a supplier.

The beta-carotene is dissolved in an organic solvent. The organic solvents suitable for use herein are known solvents for the carotenoids. The solvent must boil below boiling point of water or codistill with water. Such solvents include acetone, alcohols, ethers, hexane and methyl ethyl ketone. Other solvents also can be used, but are less preferred for food applications, for example, hydrocarbons, halogenated aliphatic hydrocarbons, petroleum ether, polyhalogenated methane e.g. chloroform, carbon tetrachloride, methylene chloride, benzene and carbon disulfide. The preferred solvent for use herein is acetone.

The compositions of the present invention which are in a powder form contain from about 0.1% to about 32%, preferably from about 1% to about 32% and more preferably from about 10% to about 32% by weight, beta-carotene, the remainder being cyclodextrins.

CYCLODEXTRIN

The cyclodextrins for use herein are water soluble derivatives of beta-cyclodextrin capable of forming inclusion complexes with beta-carotene and similar carotenoids. Beta-cyclodextrins for use in the present invention include, for example, beta-cyclodextrin, heptakis (2,6-di-O-methyl)-beta-cyclodextrin, 2-hydroxypropyl-beta-cyclodextrin, 2,3-dihydroxy propyl-beta-cyclodextrin, poly-beta-cyclodextrin or mixtures thereof. The cyclodextrins for use herein have molecular weights of at least 972 grams/mole and a water solubility of at least 1.8 grams/100 milliliters at 25° C.

The cyclodextrins are dissolved in water at a concentration of from about 0.5% to about 50%.

Preparation of Beta-Carotene/Cyclodextrin Complex

The powdered water soluble beta-carotene compositions of the present invention are prepared by initially forming an aqueous solution of cyclodextrin as described in the "cyclodextrin" section above. The beta-cyclodextrin solution is heated to a temperature of from about 45° C. to about 95° C. Separately, beta-carotene, and if desired the antioxidant, is dissolved in an organic solvent, forming a supersaturated solution of beta-carotene (b).

The solvent/beta-carotene solution (b) is slowly added to the hot solution of beta-cyclodextrin (a) with rapid stirring. The addition of the beta-carotene solution to the hot beta-cyclodextrin solution causes the excess solvent to evaporate. It is critical to the present invention that the addition of the solvent containing beta-carotene solution is added to the beta-cyclodextrin solution at a rate sufficient to prevent the accumulation of solvent in the reaction vessel. After all organic solvent has evaporated, excess beta-carotene present in the combined aqueous solution (c) is removed by any separation method known in the art (i.e. filtration, decanting, centrifugation etc.). The preferred method of separation is filtration. The remaining aqueous solution containing the complexed beta-carotene (d) is evaporated to dryness. The resulting powder can be reduced to the desired particle size by methods known in the art.

The water soluble beta-carotene powders produced herein contain from about 0.1% to about 32%, preferably from about 1% to about 32% beta-carotene.

In general, the water soluble beta-carotene composition may be included in the composition of the present invention in amounts of from about 0.001% to about 10%.

ADDITIONAL INGREDIENTS

Vitamins

Vitamins may be used to fortify the polyol polyesters of the present invention. Commercial preparations of the appropriate vitamins and/or appropriate vitamin mixtures which provide vitamins D, E and K can be used herein. Preferably the fat soluble vitamins are in an encapsulated form that increases their water solubility. The fat-soluble vitamins for use herein include vitamin D, vitamin E, and vitamin K.

The amount of the individual fat-soluble vitamins used to fortify the present compositions can vary. The amount of fat soluble vitamin used further depends on the water solubility of the vitamin. In general, the polyesters are fortified with sufficient fat-soluble vitamin to provide from about 0.08% to about 150% of the average Recommended Daily Allowance (RDA).

What is claimed is:

1. A composition of matter, comprising:

a) an edible, non-absorbable, non-digestible fat, and;

b) beta-carotene; wherein the beta-carotene is complexed with a cyclodextrin selected from the group consisting of water soluble beta-cyclodextrin or beta-cyclodextrin derivatives and mixtures thereof having a molecular weight of at least 972 grams/mole.

2. The product of claim 1 wherein the edible non-absorbable, non-digestible fat is selected from the group consisting of polyol fatty acid polyesters, diversely esterified polyols, polyol polyester polymers, polyglycerol esters, or co-crystallized blends of polyglycerol hardstock and crystal modifiers and mixtures thereof.

3. The product of claim 2 wherein the cyclodextrin is 2-hydroxypropyl-beta-cyclodextrin.

4. A composition of matter, comprising:

a) an edible, non-absorbable, non-digestible fat b) a triglyceride and;

c) beta-carotene; wherein the beta-carotene is complexed with a cyclodextrin selected from the group consisting of water soluble beta-cyclodextrin or beta-cyclodextrin derivatives or mixtures thereof having a molecular weight of at least 972 grams/mole.

* * * * *